US005788973A

United States Patent [19]
Ascione

[11] Patent Number: 5,788,973
[45] Date of Patent: Aug. 4, 1998

[54] PHOTOBLUING-RESISTANT COSMETIC/ DERMATOLOGICAL COMPOSITIONS COMPRISING TIO$_2$ PIGMENTS AND BENZOTRIAZOLE SILICONES

[75] Inventor: Jean-Marc Ascione, Hoboken, N.J.

[73] Assignee: Société L'Oréal S.A., Paris, France

[21] Appl. No.: 822,647

[22] Filed: Mar. 24, 1997

[30] Foreign Application Priority Data

Mar. 22, 1996 [FR] France .................. 96 03623

[51] Int. Cl.$^6$ ........................................ A61K 7/00
[52] U.S. Cl. ...................... 424/401; 424/59; 424/70.1
[58] Field of Search ........................ 424/401, 59, 70.1

[56] References Cited

U.S. PATENT DOCUMENTS 5,618,520  4/1997  Hansenne et al. ................ 424/59

FOREIGN PATENT DOCUMENTS 2642968  8/1990  France .
2680684  3/1993  France .
2695560  3/1994  France .

*Primary Examiner*—Thurman K. Page
*Assistant Examiner*—Lakshmi Channavajjala
*Attorney, Agent, or Firm*—Burns, Doane, Swecker & Mathis, L.L.P.

[57] ABSTRACT

Topically applicable, photobluing-resistant cosmetic/ dermatological compositions, well suited for improved photoprotection of human skin and/or the scalp against the damaging effects of UV-A and UV-B irradiation and/or for the therapeutic treatment of a disease state of the skin or scalp, comprise (a) an effective photoprotective amount of at least one titanium dioxide (nano) pigment and (b) an effective photobluing-reducing amount of at least one benzotriazole silicone.

28 Claims, No Drawings

PHOTOBLUING-RESISTANT COSMETIC/ DERMATOLOGICAL COMPOSITIONS COMPRISING TIO₂ PIGMENTS AND BENZOTRIAZOLE SILICONES

BACKGROUND OF THE INVENTION

1. Technical Field of the Invention

The present invention relates to novel photobluing-resistant cosmetic/dermatological compositions containing photoprotective amounts of titanium dioxide pigments and at least one specific benzotriazole silicone.

2. Description of the Prior Art

It is known to this art that light radiation of wavelengths of from 280 nm to 400 nm promotes tanning of human skin and that radiation of wavelengths of from 280 nm to 320 nm, i.e., UV-B, causes skin burns and erythemas which can impair the development of natural tanning and bronzing; hence, this UV-B radiation must therefore be screened or blocked from the skin.

It is also known to this art that UV-A radiation, of wavelengths of from 320 nm to 400 nm, which causes the skin to tan, also adversely affects it, in particular in the case of sensitive skin or of skin which is continually exposed to solar radiation. In particular, UV-A radiation causes a loss of skin elasticity and promotes the appearance of wrinkles, resulting in premature aging. Such irradiation promotes triggering of the erythemal reaction or accentuates this reaction in certain individuals, and can even be the cause of phototoxic or photoallergic reactions. Thus, it is desirable to also screen out the UV-A radiation.

A wide variety of sunscreens exist on the market for screening UV-A and UV-B radiation: inorganic pigments and organic screening agents. These screening agents must be able to absorb or block harmful solar radiation while at the same time remaining innocuous to the user.

To this end, metal oxide pigments are being increasingly formulated into sunscreen products and day products, in particular makeup products, on account of their scattering and reflection properties with respect to UV radiation which render same highly advantageous in terms of photoprotection. Used alone, they provide good protection against UV radiation. In combination with organic screening agents, they permit the preparation of highly photoprotective products.

In this respect, the inorganic pigment which is the most widely used today is titanium dioxide, preferably in nanopigment form, the screening or blocking properties of which are well known to this art.

However, compositions containing titanium dioxide pigments in an oxygen-free medium are observed to be unstable with respect to light, an instability which is reflected by the appearance of a blue coloration. Such photocoloration, known as photobluing, is obviously undesirable from an aesthetic standpoint.

For the purpose of limiting this photoreactivity phenomenon, surface-treated TiO₂ pigments have been described. Thus, EP-B-0,461,130 describes TiO₂ nanoparticles treated with phosphate anions. Likewise, cosmetics containing TiO₂ pigments surface-treated with silica or alumina are known. However, these treatments are expensive and difficult to carry out.

Finally, while it is indeed true that these surface treatments make it possible to reduce the photoinstability of metal oxide pigments, and in particular the photobluing of formulationms containing TiO₂ pigments, such reduction remains insufficient.

Need, therefore, continues to exist for photostable compositions containing titanium dioxide pigments. By "photostable" is intended that a given composition is not, or only slightly, subject to the photocoloring phenomenon described above.

SUMMARY OF THE INVENTION

It has now unexpectedly and surprisingly been determined that formulating, into compositions containing photoprotective amounts of TiO₂ pigments, at least one specific benzotriazole silicone significantly reduces the photobluing phenomenon intrinsically associated with such compositions.

Briefly, the present invention features reducing the photobluing of compositions containing photoprotective amounts of titanium dioxide pigments by formulating into such compositions at least one benzotriazole silicone having one of the following formulae (1) and (2):

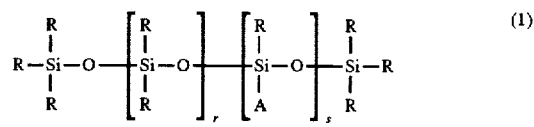

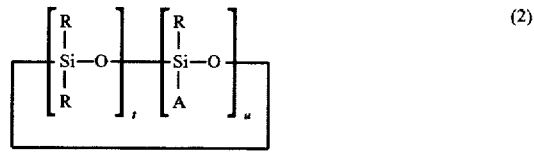

in which the radicals R, which may be identical or different, are each a $C_1-C_{10}$ alkyl, phenyl, 3,3,3-trifluoropropyl or trimethylsilyloxy radical, at least 80% by number of the radicals R being methyl radicals; r is an integer ranging from 0 to 50, inclusive; s is an integer of ranging from 1 and 20, inclusive; u is an integer of ranging from 1 and 6, inclusive; t is an integer of ranging from 0 and 10, inclusive, with the proviso that t+u is equal to or greater than 3; and A is a monovalent radical bonded directly to a silicon atom which has the following formula (3):

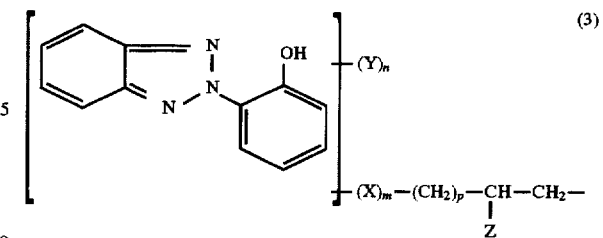

wherein the radicals Y, which may be identical or different, are each a $C_1-C_8$ alkyl radical, a halogen atom or a $C_1-C_4$ alkoxy radical, with the proviso that, in the latter event, two adjacent Y radicals on the same aromatic nucleus can together form an alkylidenedioxy radical in which the alkylidene moiety contains from 1 to 2 carbon atoms; X represents O or NH; Z represents hydrogen or a $C_1-C_4$ alkyl radical; n is an integer ranging from 0 to 3, inclusive; m is 0 or 1; and p is an integer ranging from 1 to 10, inclusive.

DETAILED DESCRIPTION OF BEST MODE AND SPECIFIC/PREFERRED EMBODIMENTS OF THE INVENTION

More particularly according to the present invention, at least one benzotriazole silicone as defined above is formulated into cosmetic and/or dermatological compositions containing photoprotective amounts of titanium dioxide pigments for decreasing the photobluing due to the presence of said pigments in said compositions.

In one specific embodiment of this invention, cosmetic and/or dermatological compositions are provided, in particular for the photoprotection of the skin and/or hair, comprising, in a cosmetically acceptable vehicle, diluent or carrier, titanium dioxide pigments and at least one benzotriazole silicone as defined above, with the proviso that the subject compositions advantageously do not contain either benzene-1,4-di(3-methylidene-10-comphorsulfonic acid) or 4,4'-methoxy-t-butyldibenzoylmethane.

Indeed, French Patent Application No. 95-05,677, assigned to the assignee hereof, describes compositions comprising benzotriazole silicones in accordance with those of the present invention in combination with benzene-1,4-di(3-methylidene-10-camphorsulfonic acid). It is indicated in this application, generally, that these compositions can also contain titanium dioxide nanopigments. However, the effect of reducing the photobluing of titanium dioxide pigments by the presence of a benzotriazole silicone is conspicuously alien to this French application.

Example 2 of FR-A-2,695,560, also assigned to the assignee hereof, describes a screening cosmetic composition comprising titanium dioxide nanopigments, a benzotriazole silicone in accordance with those of the present invention and 4,4'-methoxy-t-butyldibenzoylmethane. According to the invention of said application, the goal is to stabilize 4,4'-methoxy-t-butyldibenzoylmethane using a screening polymer of the benzatriazole silicone type. However, no reduction in the photobluing of titanium dioxide pigments via by the presence of any benzotriazole silicone is described or suggested.

The compositions according to the invention present the advantage of being very little subject to the phenomenon of photobluing commonly observed with respect to compositions containing titanium dioxide pigments.

The present invention also features a cosmetic treatment regimen for protecting the skin and/or hair against ultraviolet radiation, in particular solar radiation, comprising topically applying thereto an effective amount of at least one composition as described above.

The specific benzotriazole silicones of the present invention are selected from among the known general class of benzotriazole silicones and are those which have the following formulae:

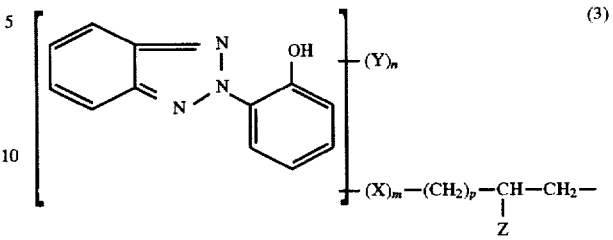

in which the radicals R, which may be identical or different, are each a $C_1-C_{10}$ alkyl, phenyl, 3,3,3-trifluoropropyl or trimethylsilyloxy radicals, at least 80% by number of the radicals R being methyl radicals; r is an integer ranging from 0 to 50, inclusive; and s is an integer ranging from 1 to 20, inclusive; u is an integer ranging from 1 to 6, inclusive; t is an integer ranging from 0 to 10, inclusive, with the proviso that t+u is equal to or greater than 3; and A is a monovalent radical bonded directly to a silicon atom which has the following formula (3):

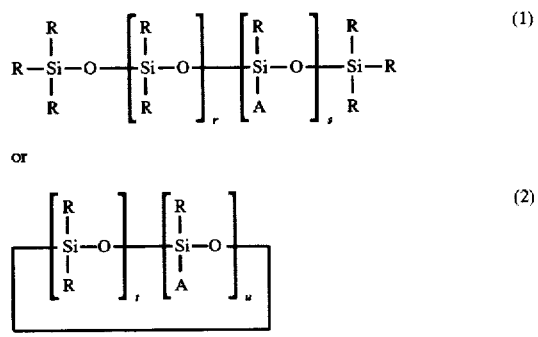

wherein the radicals Y, which may be identical or different, are each a $C_1-C_8$ alkyl radical, a halogen atom or a $C_1-C_4$ alkoxy radical, with the proviso that, in the latter event, two adjacent Y radicals on the same aromatic nucleus can together form an alkylidenedioxy radical in which the alkylidene moiety contains from 1 to 2 carbon atoms; X represents O or NH; Z represents hydrogen or a $C_1-C_4$ alkyl radical; n is an integer ranging from 0 to 3, inclusive; m is 0 or 1; and p is an integer ranging from 1 to 10, inclusive.

As will be seen from the above formula (3), the bonding of the $-(X)_m-(CH_2)_p-CH(Z)-CH_2-$ linkage to the benzotriazole nucleus, which thus provides the bonding of said benzotriazole nucleus to the silicon atom of the silicone chain, can, according to the present invention, occur at all available positions presented by the two aromatic nuclei of the benzotriazole:

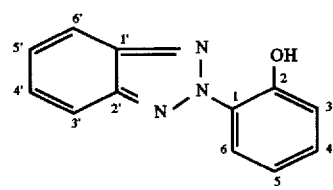

This bonding or coupling preferably is at the 3, 4, 5 (aromatic nucleus bearing the hydroxyl functional group) or 4' (benzene nucleus adjacent to the triazole ring) position and, more preferably, at the 3, 4 or 5 position. In a preferred embodiment of the invention, the coupling is at the 3 position.

Similarly, the coupling of the Y substituent unit or units can occur at all the other available positions in the benzatriazole. However, preferably, this coupling is at the 3, 4, 4', 5 and/or 6 position. In a preferred embodiment of the invention, the coupling of the Y substituent is at the 5 position.

In the above formulae (1) and (2), the alkyl radicals can be linear or branched and advantageously are selected from among methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The preferred radicals R according to the invention are the methyl, ethyl, propyl, n-butyl, n-octyl and 2-ethylhexyl radicals. More preferably, the radicals R are all methyl radicals.

It is preferable, among the compounds of above formulae (1) or (2), to use those corresponding to the formula (1), namely, diorganosiloxanes comprising a short linear chain.

More preferred, among the linear diorganosiloxanes according to the present invention, are the statistical derivatives or well-defined block derivatives exhibiting at least one, and more preferably the combination, of the following characteristics:

R is alkyl and more preferably is methyl, r ranges from 0 to 15, inclusive; s ranges from 1 to 10, inclusive, n is not zero and preferably is equal to 1 and Y is then selected from among methyl, tert-butyl or $C_1$–$C_4$ alkoxy, Z is hydrogen or methyl, m=0 or |m=1 and X=0|, p is equal to 1.

A category of compounds particularly suitable for the invention is that circumscribed by the following formula (4):

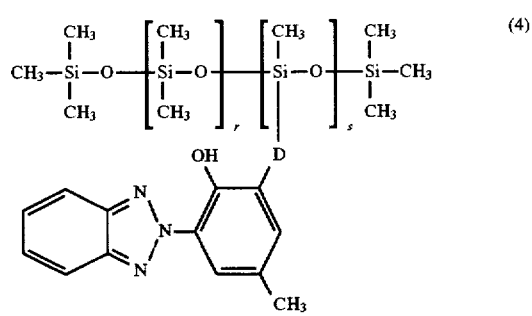

in which 0<r<10; 1<s<10; and D is the divalent radical:

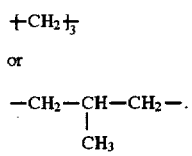

In a particularly preferred embodiment of the invention, the benzotriazole silicone is the compound (designated compound (a) hereinafter) having the formula (4) in which:

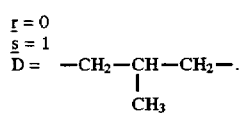

In another particularly preferred embodiment of the invention, the benzotriazole silicone is the compound (compound (b) hereinafter) having the general formula (4) in which:

r=5 s=5 and D is the divalent radical:

To prepare the silicone screening agents of formulae (1) and (2), conventional techniques can be employed, via a hydrosilylation reaction

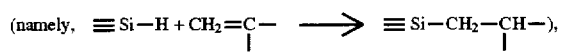

from the corresponding silicone in which, for example, all of the A radicals are hydrogen atoms. This starting silicone is hereinafter denominated derivative containing SiH. These derivatives containing SiH are compounds which are well known in the silicone arts and are generally commercially available. They are, for example, described in U.S. Pat. Nos. 3,220,972, 3,697,473 and 4,340,709. This derivative containing SiH can thus be represented either by the following formula (1a):

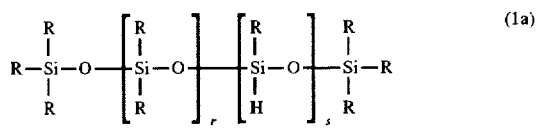

in which R, r and s are as defined above for the formula (1), or by the following formula (2a):

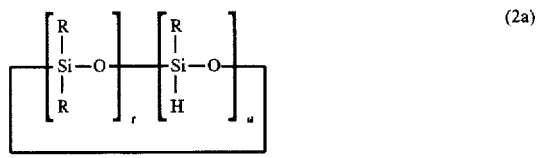

in which R, t and u are as defined above for the formula (2).

A conventional hydrosilylation reaction is therefore carried out on this derivative containing SiH of formulae (1a) or (2a), the reaction being carried out in the presence of a catalytically effective amount of a platinum catalyst, with an organic benzotriazole derivative of the following formula (3a):

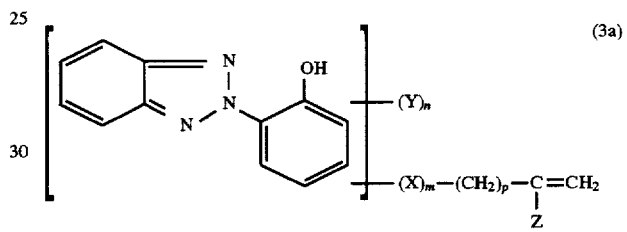

in which Y, X, Z, n, m and p are as defined above for the formula (3).

Processes which are suitable for the preparation of the compounds of above formula (3a) are, in particular, described in U.S. Pat. Nos. 4,316,033 and 4,328,346.

In addition, the details of the operating conditions to be observed in carrying out the hydrosilylation reaction between the compounds of above formula (1a) or (2a) and the compound of above formula (3a) are reported in EP-0, 392,883, hereby expressly incorporated by reference.

The compositions of the invention advantageously comprise from 0.1% to 15% by weight, preferably from 0.2% to 10% by weight, with respect to the total weight of the composition, of a benzotriazole silicone as described above.

One of the essential characteristics of the compositions of the present invention is that they contain at least one titanium dioxide pigment. The pigments of this invention are known titanium dioxide pigments commonly used in the cosmetics field as fillers or as screening agents, which can be treated or untreated. Such pigments include titanium dioxide nanopigments. By "nanopigments" are intended pigments in which the average size of the elementary particles ranges from 5 to 100 nm.

The titanium dioxide may be in rutile, anatase or amorphous form, but is preferably in rutile and/or anatase form.

The treated pigments may, for example, be treated with alumina, silica, aluminum compounds, silicon compounds, sodium compounds, iron oxides, iron esters, stearic acid or glycerol.

More particularly, the treated pigments may be titanium dioxides treated with:

(i) silica and alumina, such as the products "Microtitanium dioxide MT 500 SA" and "Microtitanium dioxide MT 100 SA" marketed by Tayca, and the products "Tioveil Fin", "Tioveil OP", "Tioveil MOTG" and "Tioveil IPM" marketed by Tioxide, (ii) alumina and aluminum stearate, such as the product "Microtitanium dioxide MT 100 T" marketed by Tayca, (iii) alumina and aluminum laurate, such as the product "Microtitanium dioxide MT 100 S" marketed by Tayca, (iv) iron oxides and iron stearate, such as the product "Microtitanium dioxide MT 100 F" marketed by Tayca, (v) silica, alumina and silicone, such as the products "Microtitanium dioxide MT 100 SAS", "Microtitanium dioxide MT 600 SAS" and "Microtitanium dioxide MT 500 SAS" marketed by Tayca, (vi) sodium hexametaphosphate, such as the product "Microtitanium dioxide MT 150 W" marketed by Tayca, (vii) octyltrimethoxysilane, such as the product "T-805" marketed by Degussa, (viii) alumina and stearic acid, such as the product "UVT-M160" marketed by Remira, (ix) alumina and glycerol, such as the product "UVT-M212" marketed by Remira, (x) alumina and silicone, such as the product "UVT-M262" marketed by Remira.

The untreated titanium dioxides may, for example, be those marketed by Tayca under the trademarks "Microtitanium dioxide MT 500 B" or "Microtitanium dioxide MT 600 B".

The titanium dioxide (nano) pigment (s) is advantageously present in the compositions according to the invention in a proportion ranging from 0.1% to 30% by weight with respect to the total weight of the composition, preferably from 0.2% to 25% by weight with respect to the total weight of the composition.

Other constituents advantageously comprising the compositions of the invention include, in particular, oils, waxy compounds, thickeners, emulsifiers or gelling agents, and are those which are conventionally employed in the cosmetics and/or dermatological fields.

By "oil" is intended a compound which is liquid at room temperature. By "wax" is intended a compound which is solid or substantially solid at room temperature and having a melting point generally greater than 35° C.

Exemplary oils include mineral oils (liquid petrolatum), vegetable oils (sweet almond, macadamia, grape seed or jojoba oil), synthetic oils, such as perhydrosqualene, fatty alcohols, acids or esters (octyl palmitate, isopropyl lanolate or triglycerides, including those of capric/caprylic acids) or oxyethylenated or oxypropylenated fatty esters and ethers, silicone oils (cyclomethicone, polydimethylsiloxanes or PDMS) or fluorinated oils, or polyalkylenes.

Exemplary waxy compounds include paraffin wax, carnauba wax, beeswax or hydrogenated castor oil.

Exemplary emulsifiers include esters of fatty acids and of polyethylene glycol (PEG), esters of fatty acids and of glycerol (glyceryl stearate) or esters of fatty acids and of sugar (sorbitan stearate), as well as their polyoxyethylenated or polyoxypropylenated derivatives, cyclomethicones and dimethicone copolyols, anionic surfactants (R or Na alkyl phosphate) or polyalkoxylated fatty alcohols.

Exemplary polyalkoxylated fatty alcohols include oxypropylenated butyl alcohols, oxyethylenated caprylic alcohols or oxyethylenated cetyl alcohols.

Exemplary thickeners include crosslinked polyacrylic acids, guar gums and celluloses, which either may or may not be modified, such as hydroxypropylated guar gum, methylhydroxyethyl cellulose, hydroxypropylmethyl cellulose or alternatively hydroxyethyl cellulose.

And exemplary gelling agents include modified clays (bentones), metal salts of fatty acids (aluminum stearate), ethylene/acrylate copolymers, silicas, polyethylenes, calcium silicates, or alternatively, ethyl cellulose.

The compositions of the present invention can also contain various ingredients conventionally used in the cosmetics, dermatological or dermopharmaceutical fields, such as coloring materials, solvents (water, alcohols and the like), preservatives, fragrances, moisturizing active principles, agents which absorb or block ultraviolet radiation (organic sunscreening agents or inorganic pigments other than titanium dioxides, in particular cerium and/or zinc oxides), pulverulent agents, bactericidal agents and/or odor absorbers.

These compositions can, in addition, contain one or more hydrophilic and preferably lipophilic cosmetic or dermatological active agents or principles, in particular for treating and/or preventing skin conditions, such as acne, mycoses, eczema, rosacea, seborrhoeic dermatitides, solar dermatitides or cutaneous aging, and conditions of the scalp. These compositions are intended for topical skin treatment.

Naturally, one skilled in this art will take care to select the possible additional compound or compounds indicated above and/or their amounts such that the advantageous properties intrinsically associated with the binary combination of the invention are not, or not substantially, detrimentally affected by the envisaged addition or additions.

The compositions of the invention can be formulated according to techniques well known to this art, in particular those for the preparation of emulsions of oil-in-water or water-in-oil type.

The subject compositions can be formulated, in particular, as simple or complex (O/W, W/O, O/W/O or W/O/W) emulsions, such as a cream, a milk, a lotion, a gel or a cream gel, as a powder or as a solid stick and can optionally be packaged as an aerosol and be provided in the form of a foam or spray.

The compositions of the invention are formulated as oil-in-water emulsions.

In order to further illustrate the present invention and the advantages thereof, the following specific examples are given, it being understood that same are intended only as illustrative and in nowise limitative.

EXAMPLES

Comparative tests were carried out in order to demonstrate the improvement attained with respect to photobluing by the introduction of a screening silicone in accordance with the invention within a composition containing titanium dioxide pigments.

Three oil-in-water emulsions A, B and C were thus prepared, each of them containing a $TiO_2$ nanopigment and a benzotriazole silicone. The emulsions A and B in accordance with the invention respectively contain the compound (a) according to the invention and the compound (b) according to the invention, as described above. The comparative emulsion C contains a benzotriazole silicone not in accordance with those of the invention (compound (c) described hereinbelow).

These three emulsions had the following composition (the amounts are expressed by weight with respect to the total weight of the composition):

| | |
|---|---|
| (a) benzotriazole silicone | 5% |
| (b) mixture of cetylstearyl alcohol and of cetylstearyl alcohol oxyethylenated with 33 EO (80/20), marketed under the trademark "Sinnovax AO" by Henkel | 7% |
| (c) glyceryl monostearate, marketed under the trademark "Geleol copeaux" by Gattefosse | 2% |
| (d) cetyl alcohol, marketed under the trademark "Lorol C 16" by Henkel | 1.5% |
| (e) $C_{12}$-$C_5$ alkyl benzoate, marketeed under the trademark "Finsolv TN" by Finetex | 15% |
| (f) polydimethylsiloxane, marketed under the trademark "Silbione 70047 V 300" by Rhone-Poulenc | 1.5% |
| (g) $TiO_2$ nanopigments, marketed under the trademark "MT 100 T" by Tayca | 5% |
| (h) glycerol | 20% |
| (i) preservative | q.s. |
| (j) water | q.s. 100% |

Emulsion A

The benzotriazole silicone was the compound (a) having the following formula:

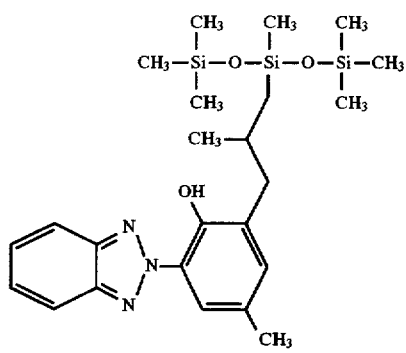

Emulsion B

The benzotriazole silicone was the compound (b) having the following formula:

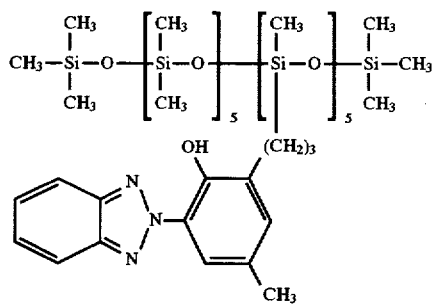

Emulsion C

The benzotriazole silicone was the compound (c) having the following formula:

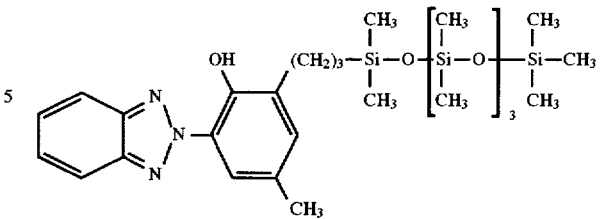

An oil-in-water emulsion D, having the same composition as the emulsions A, B and C, but not containing any benzotriazole silicone, was also prepared.

Procedure for evaluating the photobluing

For these four emulsions, the photobluing was evaluated according to the following procedure: the compositions were introduced into UV transparent plastic boxes (crystalline polystyrene boxes 50=40×6 mm) and exposed to UV radiation (Heraeus Suntest CPS) for 1 solar H. Colorimetric measurements were taken using a Minolta CM1000 calorimeter: a first measurement was taken just before exposure to the UV radiation (TO) and a second after one hour of exposure to the UV radiation (T1H).

The results are expressed in the (L, a, b) system in which L represents the luminance, a represents the red-green axis (−a=green, +a=red) and b represents the yellow-blue axis (−b=blue, +b=yellow).

In order to evaluate the photobluing, the values of interest are:

(1) ΔL ($\Delta L = L_{T1H} - L_{TO}$), which reflects the darkening of the coloration: the less negative ΔL, the less the composition has darkened, (2) Δb ($\Delta b = b_{T1H} - b_{TO}$) which reflects the bluing of the coloration: the less negative Δb, the more effective the protection against photobluing.

The results obtained are reported in the following Table:

TABLE

| Emulsion | ΔL | Δb |
|---|---|---|
| Emulsion A (invention) | −11.5 | −9.7 |
| Emulsion B (invention) | −15.4 | −11.6 |
| Emulsion C (comparative) | −20.5 | −16.1 |
| Emulsion D (comparative) | −33.1 | −22.0 |

These results clearly evidence that the emulsions containing a silicone in accordance with the invention are generally very little subject to the darkening caused by UV irradiation. They also clearly evidence that these emulsions are much less subject to photobluing than compositions which do not contain any benzotriazole silicone (emulsion D) or which contain another benzotriazole silicone (emulsion C).

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable, photobluing-resistant cosmetic/dermatological composition, comprising (a) an effective photoprotective amount of at least one titanium dioxide pigment and (b) an effective photobluing-reducing amount of at least one benzotriazole silicone having one of the following formulae (1) and (2):

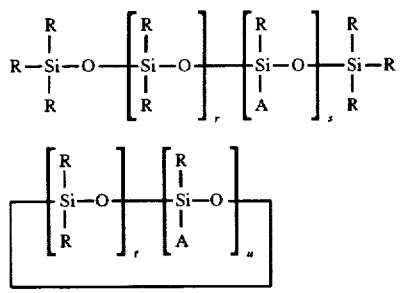

in which the radicals R, which may be identical or different, are each a $C_1$–$C_{10}$ alkyl, phenyl, 3,3,3-trifluoropropyl or trimethylsilyloxy radical, at least 80% by number of the radicals R being methyl radicals; r is an integer ranging from 0 to 50, inclusive; s is an integer of ranging from 1 and 20, inclusive; u is an integer of ranging from 1 and 6, inclusive; t is an integer of ranging from 0 and 10, inclusive, with the proviso that t+u is equal to or greater than 3; and A is a monovalent radical bonded directly to a silicon atom which has the following formula (3):

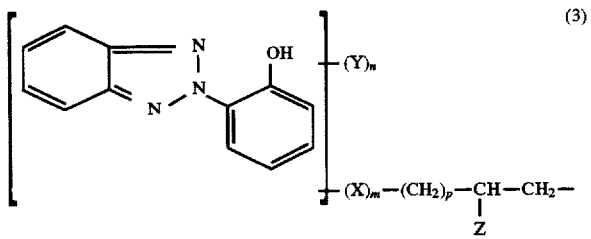

wherein the radicals Y, which may be identical or different, are each a $C_1$–$C_8$ alkyl radical, a halogen atom or a $C_1$–$C_4$ alkoxy radical, with the proviso that, in the latter event, two adjacent Y radicals on the same aromatic nucleus can together form an alkylidenedioxy radical in which the alkylidene moiety contains from 1 to 2 carbon atoms; X represents O or NH; Z represents hydrogen or a $C_1$–$C_4$ alkyl radical; n is an integer ranging from 0 to 3, inclusive; m is 0 or 1; and p is an integer ranging from 1 to 10, inclusive, wherein such composition is devoid of the compounds benzene-1,4-di(3-methylidene-10-camphorsulfonic acid) and 4,4'-methoxy-t-butyldibenzoylmethane.

2. A topically applicable, photobluing-resistant cosmetic/ dermatological composition, consisting essentially of (a) an effective photoprotective amount of at least one titanium dioxide pigment and (b) an effective photobluing-reducing amount of at least one benzotriazole silicone having one of the following formulae (1) and (2):

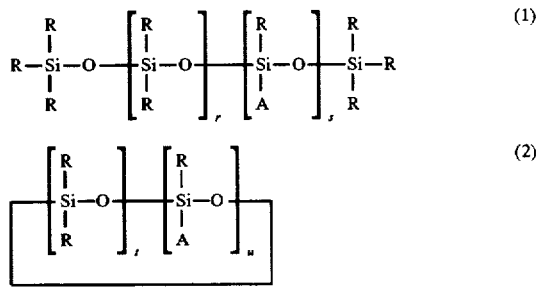

in which the radicals R, which may be identical or different, are each a $C_1$–$C_{10}$ alkyl, phenyl, 3,3,3-trifluoropropyl or trimethylsilyloxy radical, at least 80% by number of the radicals R being methyl radicals; r is an integer ranging from 0 to 50, inclusive; s is an integer of ranging from 1 and 20, inclusive; u is an integer of ranging from 1 and 6, inclusive; t is an integer of ranging from 0 and 10, inclusive, with the proviso that t+u is equal to or greater than 3; and A is a monovalent radical bonded directly to a silicon atom which has the following formula (3):

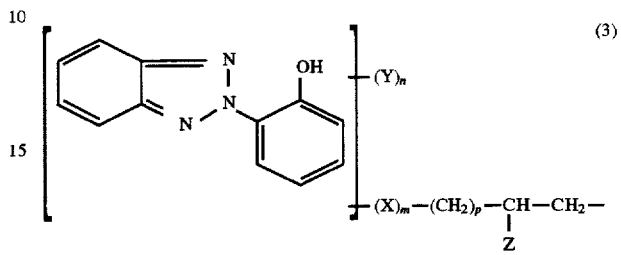

wherein the radicals Y, which may be identical or different, are each a $C_1$–$C_8$ alkyl radical, a halogen atom or a $C_1$–$C_4$ alkoxy radical, with the proviso that, in the latter event, two adjacent Y radicals on the same aromatic nucleus can together form an alkylidenedioxy radical in which the alkylidene moiety contains from 1 to 2 carbon atoms; X represents O or NH; Z represents hydrogen or a $C_1$–$C_4$ alkyl radical; n is an integer ranging from 0 to 3, inclusive; m is 0 or 1; and p is an integer ranging from 1 to 10, inclusive, wherein such composition is devoid of the compounds benzene-1,4-di(3-methylidene-10-camphorsulfonic acid) and 4,4',-methoxy-t-butyldibenzoylmethane.

3. A method for treating a disease state of the skin or scalp, comprising topically applying thereto a therapeutically effective amount of a cosmetic/dermatological composition comprising (a) an effective photoprotective amount of at least one titanium dioxide pigment and (b) an effective photobluing-reducing amount of at least one benzotriazole silicone having one of the following formulae (1) and (2):

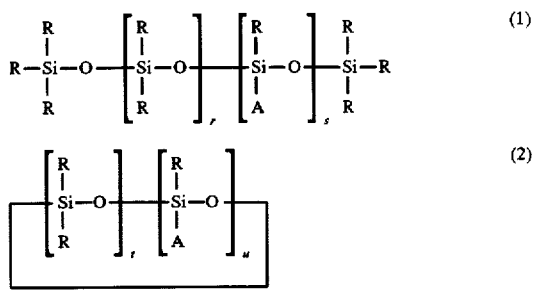

in which the radicals R, which may be identical or different, are each a $C_1$–$C_{10}$ alkyl, phenyl, 3,3,3-trifluoropropyl or trimethylsilyloxy radical, at least 80% by number of the radicals R being methyl radicals; r is an integer ranging from 0 to 50, inclusive; s is an integer of ranging from 1 and 20, inclusive; u is an integer of ranging from 1 and 6, inclusive; t is an integer of ranging from 0 and 10, inclusive, with the proviso that t+u is equal to or greater than 3; and A is a monovalent radical bonded directly to a silicon atom which has the following formula (3):

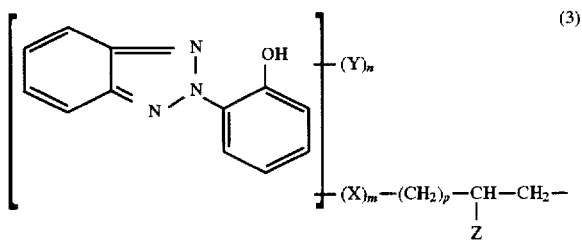

wherein the radicals Y, which may be identical or different, are each a $C_1$–$C_8$ alkyl radical, a halogen atom or a $C_1$–$C_4$ alkoxy radical, with the proviso that, in the latter event, two adjacent Y radicals on the same aromatic nucleus can together form an alkylidenedioxy radical in which the alkylidene moiety contains from 1 to 2 carbon atoms; X represents O or NH; Z represents hydrogen or a $C_1$–$C_4$ alkyl radical; n is an integer ranging from 0 to 3, inclusive; m is 0 or 1; and p is an integer ranging from 1 to 10, inclusive.

4. The cosmetic/dermatological composition as defined by claim 1, said at least one benzotriazole silicone having the formula (1).

5. The cosmetic/dermatological composition as defined by claim 1, said at least one benzotriazole silicone having the formula (2).

6. The cosmetic/dermatological composition as defined by claim 4, wherein formula (1) at least one of the following conditions is satisfied:

R is an alkyl radical;

r ranges from 0 to 15, inclusive;

s ranges from 1 to 10, inclusive;

n is other than zero;

Z is hydrogen or methyl;

m is 0, or m is 1 and X is O; and p is 1.

7. The cosmetic/dermatological composition as defined by claim 6, wherein formula (1) n is 1 and Y is methyl, tert-butyl or a $C_1$–$C_4$ alkoxy radical.

8. The cosmetic/dermatological composition as defined by claim 6, wherein formula (1) each of said conditions is satisfied.

9. The cosmetic/dermatological composition as defined by claim 4, said at least one benzotriazole silicone having the following formula (4):

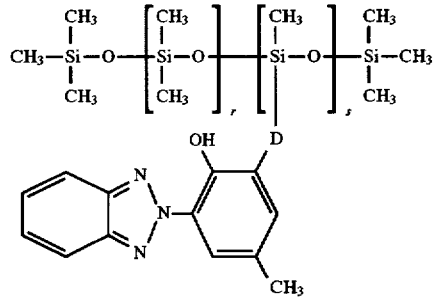

in which $0 \leq r \leq 10$; $1 \leq s \leq 10$; and D is the divalent radical:

or

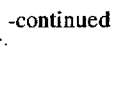

10. The cosmetic/dermatological composition as defined by claim 9, wherein formula (4) r is 0, s is 1 and D is

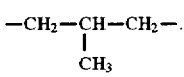

11. The cosmetic/dermatological composition as defined by claim 9, wherein formula (4) r is 5, s is 5 and D is

12. The cosmetic/dermatological composition as defined by claim 1, comprising from 0.1% to 15% by weight of said at least one benzotriazole silicone.

13. The cosmetic/dermatological composition as defined by claim 12, comprising from 2% to 10% by weight of said at least one benzotriazole silicone.

14. The cosmetic/dermatological composition as defined by claim 1, said at least one titanium dioxide pigment having an average elementary particle size ranging from 5 to 100 nm.

15. The cosmetic/dermatological composition as defined by claim 1, comprising from 0.1% to 30% by weight of said at least one titanium dioxide pigment.

16. The cosmetic/dermatological composition as defined by claim 15, comprising from 0.2% to 25% by weight of said at least one titanium dioxide pigment.

17. The cosmetic/dermatological composition as defined by claim 1, formulated into a cosmetically/dermatologically acceptable, topically applicable vehicle, diluent or carrier therefor.

18. The cosmetic/dermatological composition as defined by claim 17, comprising an oil-in-water or water-in-oil emulsion.

19. The cosmetic/dermatological composition as defined by claim 17, comprising a cream, a milk, a lotion, a gel, a cream gel, a powder, a solid stick, a foam, or a spray.

20. The cosmetic/dermatological composition as defined by claim 1, further comprising at least one oil, wax, thickener, emulsifier and/or gelling agent.

21. The cosmetic/dermatological composition as defined by claim 1, further comprising at least one colorant, solvent, preservative, fragrance, moisturizer, UV screen other than $TiO_2$, pulverulent, bactericide and/or odor absorber.

22. The cosmetic/dermatological composition as defined by claim 1, further comprising an effective amount of at least one bioactive agent for treating a disease state of the skin or scalp.

23. A treatment for protecting human skin and/or the scalp against the deleterious effects of ultraviolet irradiation, comprising topically applying thereto an effective photoprotecting amount of the cosmetic/dermatological composition as defined by claim 1.

24. A method for treating a disease state of the skin or scalp, comprising topically applying thereto a therapeutically effective amount of the cosmetic/dermatological composition as defined by claim 22.

25. The method as defined by claim 24, wherein the disease state treated is selected from the group consisting of acne, mycosis, eczema, rosacea, seborrhoeic dermatitis, solar dermatitis, skin aging and/or an affliction of the scalp.

26. A cosmetic/dermatological composition comprising (a) an effective photoprotective amount of at least one titanium dioxide pigment and (b) an effective photobluing-reducing amount of at least one benzotriazole silicone having one of the following formulae (1) and (2):

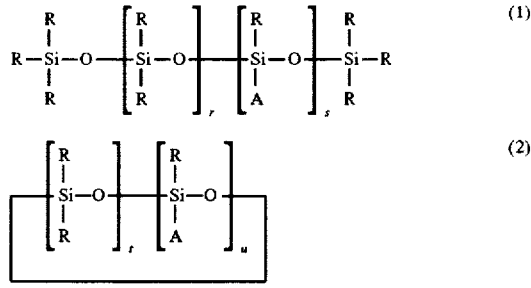

in which the radicals R, which may be identical or different, are each a $C_1-C_{10}$ alkyl, phenyl, 3,3,3-trifluoropropyl or trimethylsilyloxy radical, at least 80% by number of the radicals R being methyl radicals; r is an integer ranging from 0 to 50, inclusive; s is an integer of ranging from 1 and 20, inclusive; u is an integer of ranging from 1 and 6, inclusive; t is an integer of ranging from 0 and 10, inclusive, with the proviso that t+u is equal to or greater than 3; and A is a monovalent radical bonded directly to a silicon atom which has the following formula (3):

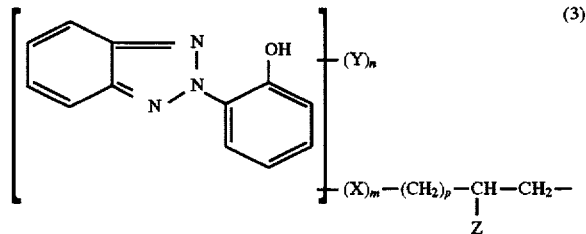

wherein the radicals Y, which may be identical or different, are each a $C_1-C_8$ alkyl radical, a halogen atom or a $C_1-C_4$ alkoxy radical, with the proviso that, in the latter event, two adjacent Y radicals on the same aromatic nucleus can together form an alkylidenedioxy radical in which the alkylidene moiety contains from 1 to 2 carbon atoms; X represents O or NH; Z represents hydrogen or a $C_1-C_4$ alkyl radical; n is an integer ranging from 0 to 3, inclusive; m is 0 or 1; and p is an integer ranging from 1 to 10, inclusive, further comprising an effective amount of at least one bioactive agent for treating a disease state of the skin or scalp.

27. A treatment for protecting human skin and/or the scalp against the deleterious effects of ultraviolet irradiation, comprising topically applying thereto an effective photoprotecting amount of a cosmetic/dermatological composition, comprising (a) an effective photoprotective amount of at least one titanium dioxide pigment and (b) an effective photobluing-reducing amount of at least one benzotriazole silicone having one of the following formulae (1) and (2):

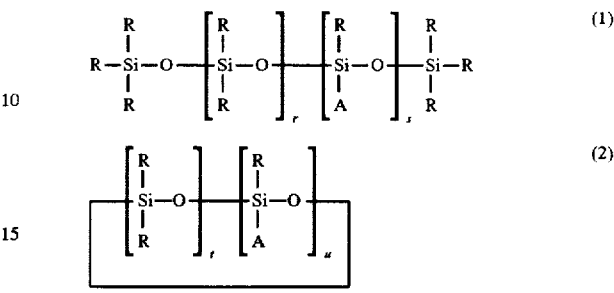

in which the radicals R, which may be identical or different, are each a $C_1-C_{10}$ alkyl, phenyl, 3,3,3-trifluoropropyl or trimethylsilyloxy radical, at least 80% by number of the radicals R being methyl radicals; r is an integer ranging from 0 to 50, inclusive; s is an integer of ranging from 1 and 20, inclusive; u is an integer of ranging from 1 and 6, inclusive; t is an integer of ranging from 0 and 10, inclusive, with the proviso that t+u is equal to or greater than 3; and A is a monovalent radical bonded directly to a silicon atom which has the following formula (3):

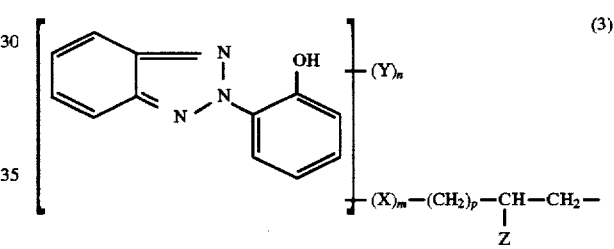

wherein the radicals Y, which may be identical or different, are each a $C_1-C_8$ alkyl radical, a halogen atom or a $C_1-C_4$ alkoxy radical, with the proviso that, in the latter event, two adjacent Y radicals on the same aromatic nucleus can together form an alkylidenedioxy radical in which the alkylidene moiety contains from 1 to 2 carbon atoms; X represents O or NH; Z represents hydrogen or a $C_1-C_4$ alkyl radical; n is an integer ranging from 0 to 3, inclusive; m is 0 or 1; and p is an integer ranging from 1 to 10, inclusive.

28. The method of claim 3, wherein the disease state treated is selected from the group consisting of acne, mycosis, eczema, rosacea, seborrhoeic dermatitis, solar dermatitis, skin aging and/or an affliction of the scalp.

* * * * *